(12) United States Patent
Spaide

(10) Patent No.: US 7,648,239 B2
(45) Date of Patent: Jan. 19, 2010

(54) AUTOFLUORESCENCE PHOTOGRAPHY USING A FUNDUS CAMERA

(76) Inventor: Richard Spaide, 530 E. 72nd St., Apt. 15E, New York, NY (US) 10021

(*) Notice: Subject to any disclaimer, the term of this patent is extended or adjusted under 35 U.S.C. 154(b) by 0 days.

(21) Appl. No.: 11/742,672

(22) Filed: May 1, 2007

(65) Prior Publication Data

US 2008/0273172 A1 Nov. 6, 2008

(51) Int. Cl.
*A61B 3/14* (2006.01)
*A61B 3/10* (2006.01)

(52) U.S. Cl. .................. 351/206; 351/210; 351/221
(58) Field of Classification Search .......... 351/200, 351/205–206, 210, 221
See application file for complete search history.

(56) References Cited

U.S. PATENT DOCUMENTS

| | | | |
|---|---|---|---|
| 6,013,034 A * | 1/2000 | Fernandes Da Cunha Vaz et al. | 600/476 |
| 6,478,424 B1 | 11/2002 | Grinvald et al. | |
| 2005/0094099 A1* | 5/2005 | Newman et al. | 351/205 |
| 2005/0182327 A1* | 8/2005 | Petty et al. | 600/476 |
| 2008/0266520 A1 | 10/2008 | Spaide | |

OTHER PUBLICATIONS

Delori FC, et al. In vivo fluorescence of the ocular fundus exhibits retinal pigment epithelium lipofuscin characteristics. Invest Ophthalmol Vis Sci 1995;36:718-729.

von Ruckmann A, Fitzke FW, Bird AC. Distribution of fundus autofluorescence with a scanning laser ophthalmoscope. Br J Ophthalmol 1995;;79:407-412.

Eldred GE, Katz ML. Fluorophores of the human retinal pigment epithelium: separation and spectral characterization. Exp Eye Res 1988;47:71-86.

Eldred GE. Lipofuscin fluorophore inhibits lysosomal protein degradation and may cause early stages of . . . Gerontology 1995:41 (Suppl 2):15-28.

Gaillard ER, Atherton SJ, Eldred G, Dillon J. Photophysical studies on human retinal lipofuscin. Photochem Photobiol 1995;61:448-453.

Li W, Yanoff M, Li Y, He Z. Artificial senescence of bovine retinal pigment epithelial cells induced by . . . Mech Ageing Dev 1999 22;110:137-155.

Yin D. Biochemical basis of lipofuscin, ceroid, and age-pigment-like fluoreophores. Free Radic Biol Med 1996; 21: 871-888.

(Continued)

*Primary Examiner*—Scott J Sugarman
*Assistant Examiner*—Dawayne A Pinkney
(74) *Attorney, Agent, or Firm*—Wolff & Samson PC

(57) ABSTRACT

Methods and apparatus for taking autofluorescence images with a fundus camera capable of a field of view of at least 30 degrees and preferably 50 degrees or more using high quality thin film optical interference filters. In one embodiment, a filter set is disclosed for achieving this functionality. Using these methods and/or apparatus, a practitioner can (among other procedures, which are described) take high-quality autofluorescence images of the fundus using a CCD camera that does not have to be cooled, take such images without exciting damaging photochemical reactions in the retina, detect accumulation of fluorophores in the retina prior to the significant accumulation of fluorophores in the retinal pigment epithelium, and topographically localize and quantitate retinal abnormalities and retinal pigment epithelium abnormalities.

28 Claims, 6 Drawing Sheets

OTHER PUBLICATIONS

Reinboth JJ. Lipofuscin in the retina: quantitative assay for an unprecedented autofluorescent compound (pyridinium bis-retinoid, A2-E) . . . Exp Eye Res. 1997;65:639-643.

Suter M, Reme, et al. Age-related macular degeneration. The lipofuscin component n-retinyl-n-retinylidene ethanolamine . . . J Biol Chem 2000 15;275:39625-30.

Sparrow JR,. The lipofuscin fluorophore A2E mediates blue light-induced damage to retinal pigmented epithelial cells. Invest Ophthalmol Vis Sci. 2000;41:1981-1989.

Liu J, . The biosynthesis of A2E, a fluorophore of aging retina, involves the formation of the precursor, A2-PE, in the photoreceptor . . . J Biol Chem. 2000 22;275:29354-29360.

Fishkin N, Jang YP, Itagaki Y, et al. A2-rhodopsin: a new fluorophore isolated from photoreceptor outer segments. Org Biomol Chem. 2003 7;1:1101-1105.

Spaide RF, Klancnik Jr JM. Fundus autofluorescence and central serous chorioretinopathy. Ophthalmology 2005; 112: 825-833.

Spaide RF, Noble K, Morgan A, Freund KB. Vitelliform macular dystrophy. Ophthalmology 2006;113:1392-400.

Wing GL,. The topography and age relationship of lipofuscin concentration in the retinal pigment epithelium. Invest Ophthalmol Vis Sci 1978;17:601-607.

Delori FC, Fleckner MR, Goger DG, et al. Autofluorescence distribution associated with drusen in age-related macular degeneration. Invest Ophthalmol Vis Sci. 2000;41:496-504.

Spaide RF. Fundus autofluorescence and age-related macular degeneration. Ophthalmology 2003;110:392-399.

Reichman Jay. Handbook of Optical Filters for Fluorescence Microscopy. HB1.2. Chroma Technology Corp. Dec. 2007.

Omega Optical, "Glossary of Terms," https://www.omegafilters.com/index.php?page=tech_glossary downloaded on Jan. 14, 2009.

PCT Search Report corresponding to PCT App. No. PCT/US07/67858 filed Apr. 7, 2008.

\* cited by examiner

AUTOFLUORESCENCE PHOTOGRAPHY USING A FUNDUS CAMERA

BACKGROUND OF THE INVENTION

1. Field of the Invention

The Invention is in the field of opthalmology, and concerns the use of a fundus camera to take autoflourescence images using high performance thin film optical interference filters.

2. Background of the Related Art

The diagnosis and treatment of retinal diseases is highly dependent on the ability to image the ocular fundus. Monochromatic and color photography provide means to record the fundus photographically. Fluorescein angiography affords a way to investigate and document vascular anatomy and physiology of the eye. In this test fluorescein dye is injected into the circulation, (usually in the arm) and the passage of the dye is photographed as it traverses the ocular circulation. The fluorescein dye passes through the vessels in the eye and can be recorded photographically.

FIG. 1 shows illustrative spectra for purposes of the following discussion, including lipofuscin, fluorescein and indocyanine green excitation and emission spectra, as well as the excitation and barrier filters for autofluorescence detection as employed by commercial scanning laser opthalmoscope systems. The lens autofluorescence shown is for an excitation of 485 nm, for comparison purposes. To image the fluorescein dye two optical filters are used. One filter, called an excitation filter, uses wavelengths generally centered between 490-500 nm to excite fluorescein. As shown in spectral curve 101, fluorescein can absorb, and potentially produce fluorescence from, wavelengths up to 530 nm. The other filter, called a barrier filter, is a low-pass filter having an upper cutoff at about 500 nm. Fluorescein fluoresces at a peak between 520-530 nm as illustrated by the spectral curve 102. Indocyanine green angiography (for which the applicable excitation (103) and emission (104) spectra are also shown in FIG. 1) is done in a somewhat similar fashion in that the dye is injected, and the fluorescence of the dye, which occurs in the near infra-red region (peaking at 825 to 835 nm), is photographed. With these dyes we could directly visualize the vessels of the ocular fundus and could indirectly obtain information about other layers of the fundus.

Another approach to imaging the fundus would be to cause naturally occurring fluorophores in the fundus to fluoresce and then record that fluorescence. There is a waste material that accumulates within cells, namely lipofuscin, that is highly autofluorescent.[1-5] (All bibliographic references are listed by number in Table I.) Lipofuscin accumulates in cells as a normal consequence of life. Increased amounts of lipofuscin can accumulate through a variety of mechanisms. In many cell types, oxidative damage can increase the amount of lipofuscin present.[6,7] Lipofuscin accumulation can occur in a number of different inherited diseases. In the eye, lipofuscin accumulates through a novel mechanism within a cell monolayer called the retinal pigment epithelium (RPE). The retina is the light sensitive structure within the eye. On the bottom surface of the retina there are photoreceptors, which are cells that have numerous small flat discs called outer segments. These outer segments are composed of retinoids used in the actual detection of light, proteins, and polyunsaturated fatty acids. Normal retinal function leads to the accumulation of autofluorescent fluorophores. These molecular components are capable of being damaged by light and oxygen. The photoreceptors shed the outer segments and the shed outer segments are phagocytized by the retinal pigment epithelium.

The undamaged fatty acids and retinoids are removed from the outer segments and are recycled by the retinal pigment epithelium. However, a portion of the material within the outer segments is damaged. Some of this material proves to be very difficult for the retinal pigment epithelial cell to digest. This material is segregated by the cell into structures known as liposomes which contain the material lipofuscin. One important component of lipofuscin in retinal pigment epithelial cells is a molecule called A2E, which is formed from two molecules of trans-retinal and one molecule of phosphatidylethanolamine.[8] The composition of lipofuscin in retinal pigment epithelial cells is somewhat different than lipofuscin found in other cells of the body because of the unique job of the retinal pigment epithelium in processing the photoreceptor outer segments. Components of lipofuscin inhibit lysosomal protein degradation,[4] are photoreactive,[5] are capable of producing a variety of reactive oxygen species and other radicals,[5] are amphiphilic, may induce apoptosis of the RPE,[9] and mediates blue light induced RPE apoptosis.[10]

There are sources of autofluorescence (i.e., fluorophores) within the eye other than lipofuscin. Precursors of A2E, such as A2PE-$H_2$, A2PE, and A2-rhodopsin, all of which are autofluorescent, form in outer segments prior to phagocytosis by the RPE,[11,12] There is not a significant accumulation of the autofluorescent material within the retina unless there is some disease process that limits the retinal pigment epithelium's ability to phagocytize the outer segments.[13,14] The fluorescence spectra for the precursors of A2E peaks at wavelengths longer than A2E. The accumulation of autofluorescence within the ocular fundus occurs from fairly predictable mechanisms. By imaging the autofluorescence we can obtain not only anatomic information from the lipofuscin that is in retinal pigment epithelial cells, but we can make inferences about functional aspects of these retinal pigment epithelial cells as well.

Imaging Autofluorescence

Lipofuscin can be made to fluoresce and has a broad emission band (105 in FIG. 1) ranging from about 500 to beyond 750 nm.[1] In opthalmology this intrinsic fluorescence is called autofluorescence to differentiate this process from that seen from administered dyes like fluorescein or indocyanine green. The intensity of fundus autofluorescence parallels the amount and distribution of lipofuscin.[1,15,16]

If we shine excitation light into the eye to excite the lipofuscin, the resultant fluorescence can be detected. The major problem with such an approach is that there are structures in the eye in front of the retina that also fluoresce. The main culprit in this regard is the crystalline lens, which has a broad band of fluorescence (106 in FIG. 1) secondary to principally blue, but also green fluorophores especially as it develops nuclear sclerosis with age. The fluorescent emission from the crystalline lens varies with the excitation light used, the age of the patient, the amount of nuclear sclerosis, and the concurrent diseases that may be present such as diabetes. The lens fluorescence has a broad peak ranging from 500 to about 550 nm for the commonly used wavelengths for autofluorescence photography of the fundus. Therefore autofluorescence of the crystalline lens overlaps the fluorescence produced by fluorescein. Crystalline lens autofluorescence causes fluorescein angiograms to look washed out when taken of an eye with nuclear sclerosis—the autofluorescence of the lens adds to the fluorescence coming from the fundus to produce an image with low contrast. To produce useful autofluorescence images we need to be able to either reject or bypass the fluorescence of the lens.

Scanning laser opthalmoscopes have a confocal capability where only conjugate points on the fundus are imaged. Points not lying on the conjugate planes are rejected. So the autofluorescence of the lens can be rejected by a scanning laser opthalmoscope. This allows confocal scanning laser opthalmoscopes to use excitation 201 and barrier 202 filters (as represented in FIG. 2) similar to that used in fluorescein angiography to obtain autofluorescence photographs. The gain is turned up and usually a number of images are taken and then averaged to obtain a final image with less noise. However, autofluorescent images cannot be taken if a patient has previously received fluorescein dye. Increasing attenuation of the excitation light occurs with increasing nuclear sclerosis. The photographs obtained with a scanning laser are quite noisy and it is customary to average several images together to reduce the noise present. The software routines that perform this function commonly normalize the image, changing the grayscale values in the process. This makes objective measurement of grayscale values with the commercially available scanning laser impossible. The wavelengths commonly used for autofluorescence determination by the commercially available scanning laser opthalmoscope are absorbed by the macular pigment, which limits its ability to accurately image the central macula.

Delori, et al. used a 550 nm excitation filter with a glass absorbing filter centered at 590 nm. The camera system used a CCD camera cooled to −20 degrees C. and had a restricted field of view of 13 degrees " . . . to minimize the loss in contrast caused by light scattering and fluorescence from the crystalline lens." This system was capable of imaging autofluorescence, but the published images had low contrast and a 13 degree field of view is not acceptable for clinical practice.[17]

The details of a fundus camera system that I previously developed for photographing autofluorescence in the retina are published.[18] The applicable spectral characteristics are illustrated in FIG. 3, including the corresponding curves 301, 302 for the excitation and barrier filters, respectively, of that publication. This camera system used a bandpass filter centered at about 580 nm (yellow-orange) for excitation and a bandpass filter centered at about 695 nm (near infrared that extended into the infrared wavelengths) as a barrier filter. The wavelengths used are not expected to show much attenuation from nuclear sclerosis. Since the lens fluorescence occurs with wavelengths shorter than the upper cut-off of the barrier filter, lens autofluorescence is usually not much of a problem, unless the patient has severe degrees of nuclear sclerosis. The limitations of this system for autofluorescence include all of those a typical fundus camera would face, particularly for patients with small pupils. The absorption of fluorescein extends to at least 530 nm and thus the published filter stimulates fluorescein. The excitation filter used a metal dielectric coating to block the far infrared portions of the spectrum, which caused a reduction in the transmission of the desired wavelengths by about one-half. The barrier filter was placed into the near infrared region, which has some disadvantages. The first is that this range of wavelengths is on the far, declining, edge of the fluorescence spectrum of lipofuscin. The second is that the optical performance of the camera and the eye is better adapted to visible wavelengths. The third disadvantage of this filter system was that the far infrared portion of the returning light was not blocked by the barrier filter. Longer wavelengths of light can penetrate through tissue to greater extent than shorter wavelengths. Longer wavelength fluorescence originating from deeper levels of tissue can decrease the contrast of the images acquired from more proximal layers of interest, thus degrading the image. The fourth problem was that the design goal of the older filters was to have less than 1% transmission at the crossover wavelengths between the lower boundary of the excitation filter and the upper boundary of the blocking filter. This still provided for the opportunity to have a significant cross-talk.

Thus, in view of the disadvantages and limitations of the current approaches, there remains a need for better methods and apparatus for autofluorescence imaging in the eye.

The state of the art is summarized in the references shown in Table I.

TABLE I

REFERENCES

1 Delori FC, Dorey CK, Staurenghi G, et al. In vivo fluorescence of the ocular fundus exhibits retinal pigment epithelium lipofuscin characteristics. Invest Ophthalmol Vis Sci 1995; 36: 718-
2 von Ruckmann A, Fitzke FW, Bird AC. Distribution of fundus autofluorescence with a scanning laser ophthalmoscope. Br J Ophthalmol 1995;; 79: 407-12.
3 Eldred GE, Katz ML. Fluorophores of the human retinal pigment epithelium: separation and spectral characterization. Exp Eye Res 1988; 47: 71-86.
4 Eldred GE. Lipofuscin fluorophore inhibits lysosomal protein degradation and may cause early stages of macular degeneration. Gerontology 1995; 41 (Suppl 2): 15-28.
5 Gaillard ER, Atherton SJ, Eldred G, Dillon J. Photophysical studies on human retinal lipofuscin. Photochem Photobiol 1995; 61: 448-53.
6 Li W, Yanoff M, Li Y, He Z. Artificial senescence of bovine retinal pigment epithelial cells induced by near-ultraviolet in vitro. Mech Ageing Dev 1999 22; 110: 137-55
7 Yin D. Biochemical basis of lipofuscin, ceroid, and age-pigment-like fluoreophores. Free Radic Biol Med 1996; 21: 871-888.
8. Reinboth JJ, Gautschi K, Munz K, Eldred GE, Reme CE. Lipofuscin in the retina: quantitative assay for an unprecedented autofluorescent compound (pyridinium bis-retinoid, A2-E) of ocular age pigment. Exp Eye Res. 1997; 65: 639-43.
9 Suter M, Reme C, Grimm C, et al. Age-related macular degeneration. The lipofuscin component n-retinyl-n-retinylidene ethanolamine detaches proapoptotic proteins from mitochondria and induces apoptosis in mammalian retinal pigment epithelial cells. J Biol Chem 2000 15; 275: 39625-30.
10 Sparrow JR, Nakanishi K, Parish CA. The lipofuscin fluorophore A2E mediates blue light-induced damage to retinal pigmented epithelial cells. Invest Ophthalmol Vis Sci. 2000; 41: 1981-9.

TABLE I-continued

REFERENCES

11. Liu J, Itagaki Y, Ben-Shabat S, Nakanishi K, Sparrow JR. The biosynthesis of A2E, a fluorophore of aging retina, involves the formation of the precursor, A2-PE, in the photoreceptor outer segment membrane. J Biol Chem. 2000 22; 275: 29354-60.
12. Fishkin N, Jang YP, Itagaki Y, et al. A2-rhodopsin: a new fluorophore isolated from photoreceptor outer segments. Org Biomol Chem. 2003 7; 1: 1101-5.
13. Spaide RF, Klancnik Jr JM. Fundus autofluorescence and central serous chorioretinopathy. Ophthalmology 2005; 112: 825-833.
14. Spaide, RF, Noble K, Morgan A, Freund KB. Vitelliform macular dystrophy. Ophthalmology 2006; 113: 1392-400.
15. Wing GL, Blanchard GC, Weiter JJ. The topography and age relationship of lipofuscin concentration in the retinal pigment epithelium. Invest Ophthalmol Vis Sci 1978; 17: 601-7
16. von Ruckmann A, Fitzke FW, Bird AC. Distribution of fundus autofluorescence with a scanning laser ophthalmoscope. Br J Ophthalmol 1995; 79: 407-12
17. Delori FC, Fleckner MR, Goger DG, et al. Autofluorescence distribution associated with drusen in age-related macular degeneration. Invest Ophthalmol Vis Sci. 2000; 41: 496-504.
18. Spaide RF. Fundus autofluorescence and age-related macular degeneration. Ophthalmology 2003; 110: 392-9.

SUMMARY OF THE INVENTION

The present invention concerns methods of taking autofluorescence images with a fundus camera capable of a field of view of at least 30 degrees and preferably 50 degrees or more using high quality thin film optical interference filters. In one embodiment, autofluorescence photographs are taken by exciting the lipofuscin present in the eye by shining an excitation light onto the eye through an excitation filter; detecting the resulting fluorescence of the lipofuscin through a barrier filter; and recording the autofluorescent image.

Preferably, the filters employed are interferometric band-pass filters with steep cut-on, cut-off and flat transmission band. Preferably, the excitation filter has a band-pass range of about 535-585 nm and the barrier filter has a band-pass range of about 605-715 nm. To improve the signal-to-noise ratio, the excitation and barrier filters should preferably meet tight transmission and blocking tolerances with a rejection of greater than $10^7$. In practice, the filter specifications for bandwidth are nominal and actual values can vary within manufacturing tolerances. This is a practical limit on the proximity of the lower cut-off for the excitation and the upper cut-on of the barrier filter.

The invention may be applied to taking images using low flash illumination, and may be used to estimate the amount of macular pigment. The wavelengths used for the barrier filter are suitable for imaging the lipofuscin precursors as they accumulate in the retina.

The invention also concerns the use of a photographic system comprising a fundus camera, certain filters, a CCD camera which does not necessarily have to be cooled, and a computer system for processing, saving, and displaying the resultant images as more fully described in the detailed description.

Other features and advantages of the invention will be apparent from the description of the drawings and the detailed description which follow.

DETAILED DESCRIPTION

The following is a description of several preferred embodiments of various aspects of the invention. These embodiments are illustrative only. The invention is limited only by the scope of the claims which are appended hereto, and is by no means limited to particular examples described below.

The newly developed fundus camera-based system for autofluorescence photographs uses filters designed to avoid autofluorescence from the lens.

Figure 4:
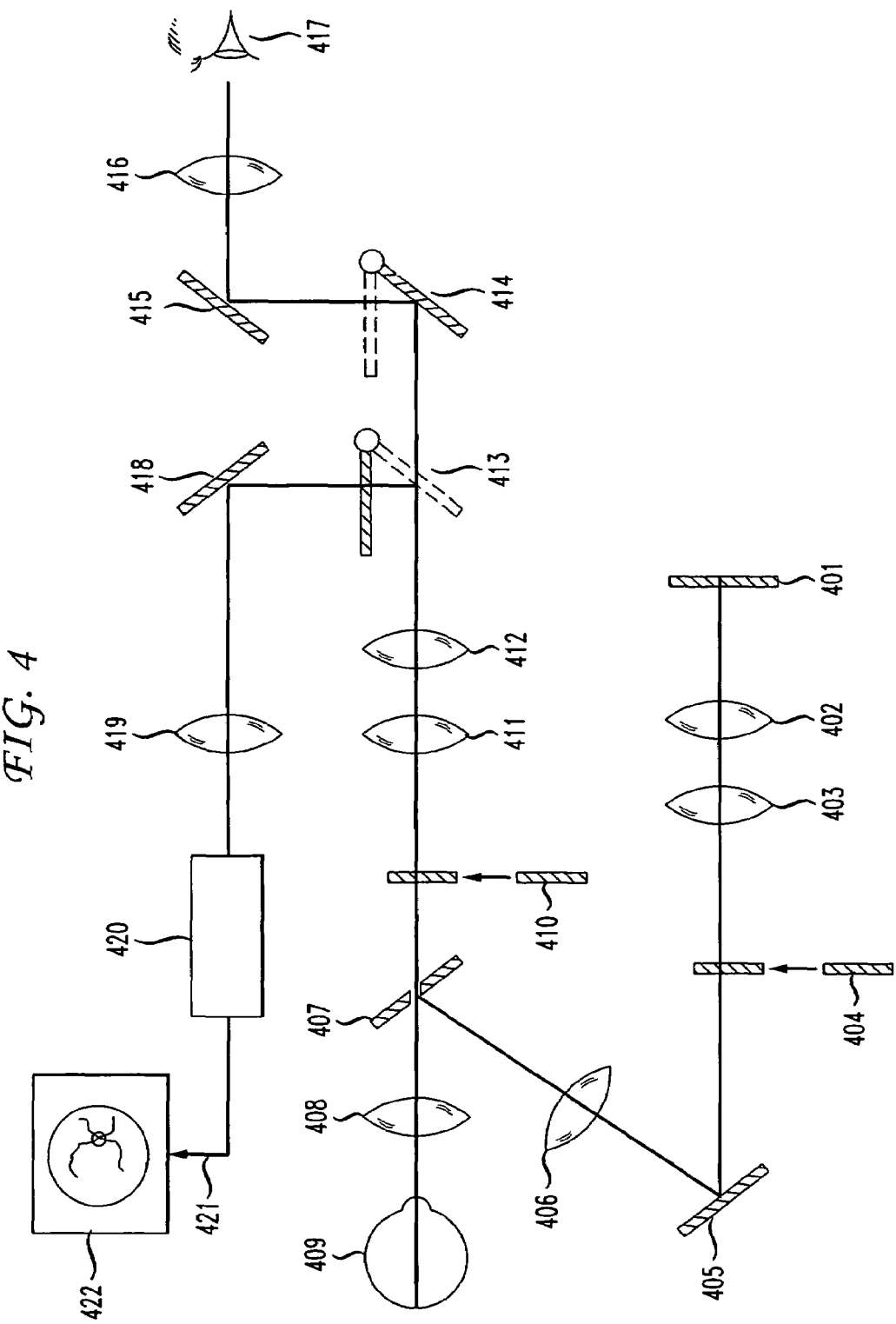
FIG. 4 is a simplified schematic diagram showing a fundus camera-based system for practicing the present invention.

One embodiment of a fundus camera-based system for practicing the methods of the present invention is shown in FIG. 4. FIG. 4 is a simplified schematic diagram showing a fundus camera-based system for practicing the present invention, and an exemplary placement of the filters used for autofluorescence. In FIG. 4, 401 is the light source, which is generally a halogen light for viewing and a xenon flash lamp for photography. Light produced travels through condenser 402 and relay 403 lenses to reach the exciter filter at 404. This filter can be shifted into the optical path as need for green monochromatic or autofluorescence photography. The light is reflected by mirror 405 through relay lens 406 to the holed or fenestrated mirror 407. This directs light toward the eye through objective lens 408 into the eye 409. Light returning from the eye is focused by the objective lens through the hole in mirror 407. The barrier filter 410 is positioned such that it can be brought into position for autofluorescence or deep-red photographs. The light passes through focusing 411 and imaging lenses 412 and passes through the area occupied by a switching mirror 413. When the operator is viewing the fundus, light is directed to mirrors 414 and 415 through the eyepiece 416 to the operator's eye 417. When a photograph is taken the switching mirror position drops down and light is reflected to mirror 418 through relay lens 419 to the image-recording device 420. While this conceivably could be a film camera, in practical use it is a CCD camera connected electronically 421 to a computer and display 422. Images can be recorded digitally by frame capture.

Figure 1:
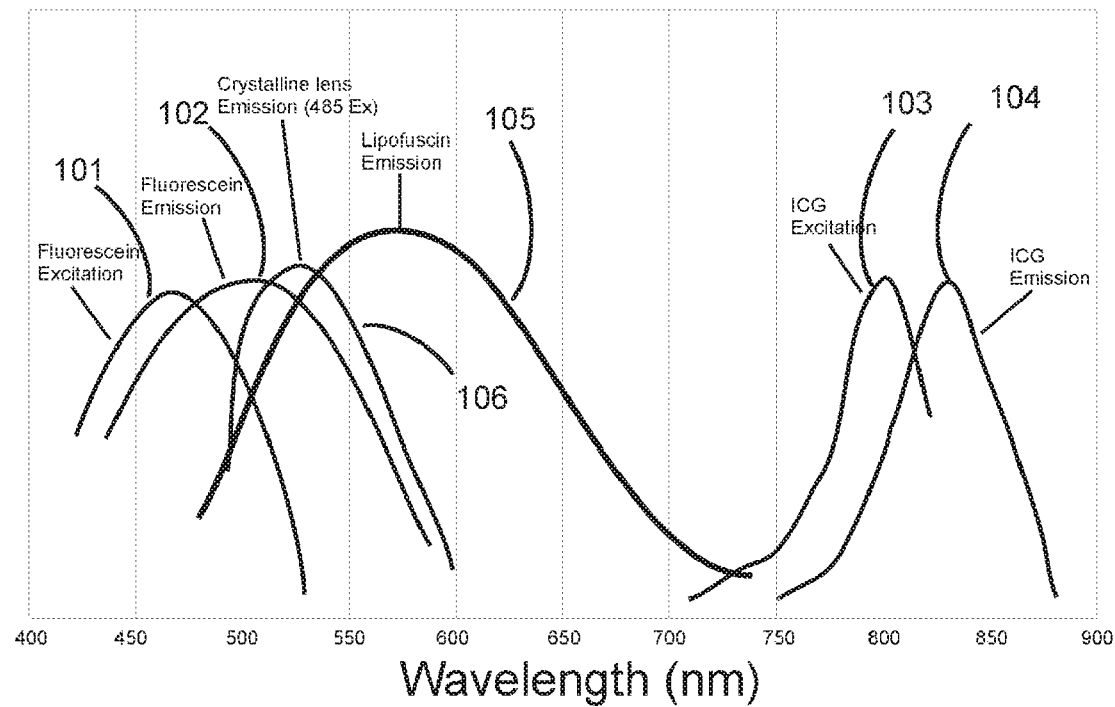
FIG. 1 shows illustrative spectra for lipofuscin, fluorescein and indocyanine green excitation and emission spectra, an example spectrum for lens autofluorescence.
Figure 2:
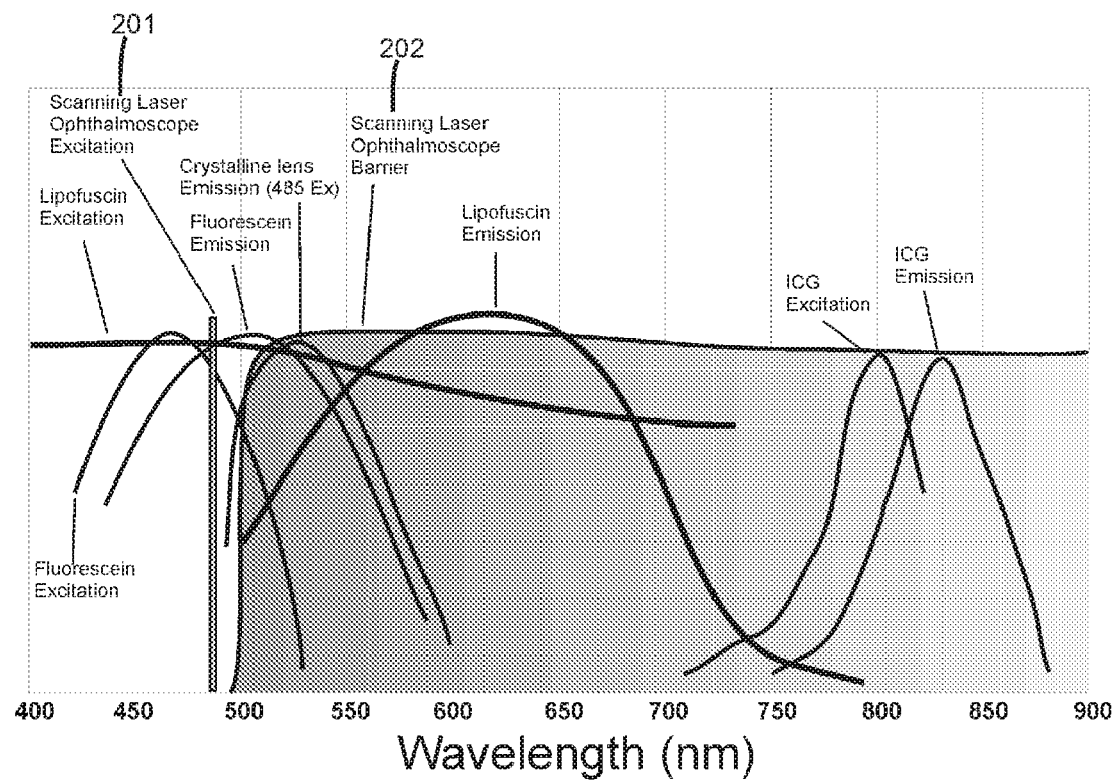
FIG. 2 shows the illustrative spectra of FIG. 1, but with illustrative spectra for the commercially available scanning laser opthalmoscopic system's excitation and barrier wavelengths.
Figure 3:
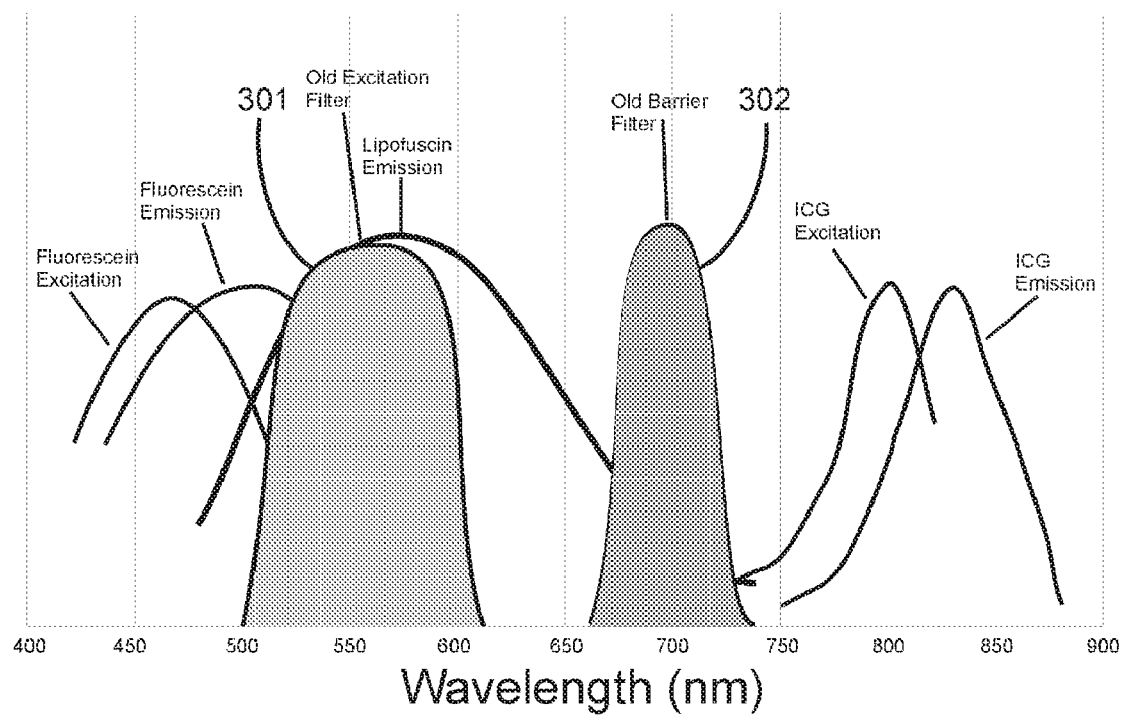
FIG. 3 shows the illustrative spectra of FIG. 1, but with the excitation and barrier filters for autofluorescence detection as previously described by Spaide (Opthalmology 2003).
Figure 5:
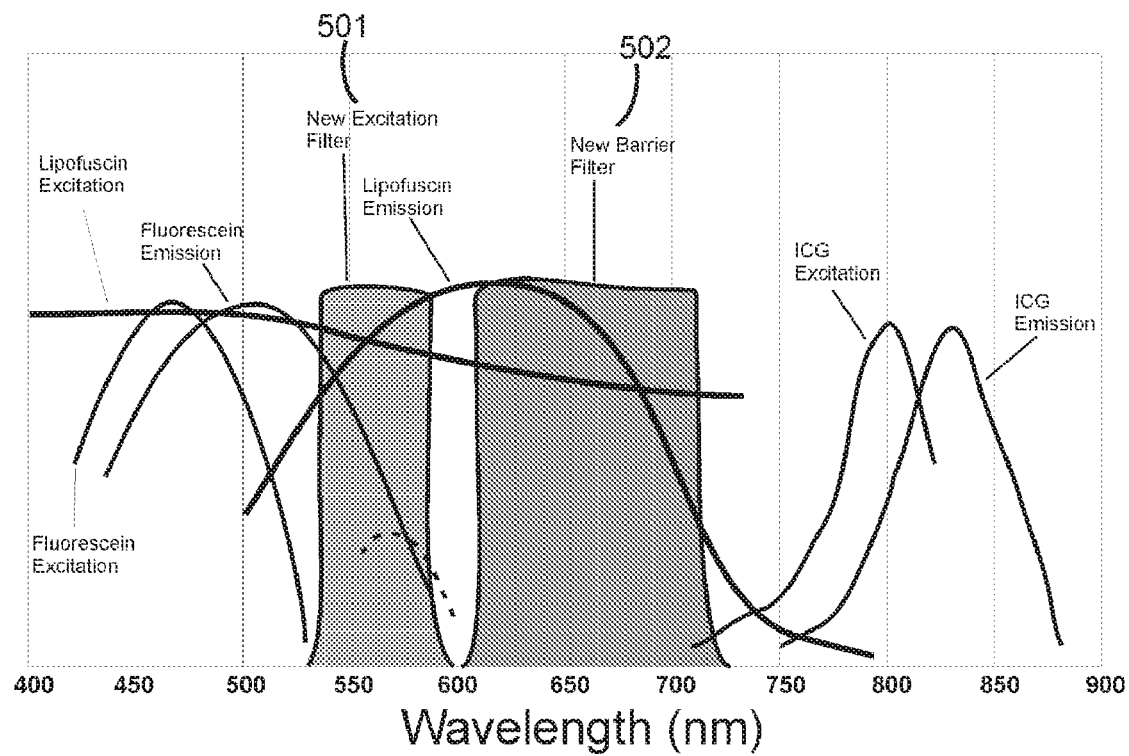
FIG. 5 shows the illustrative spectra of FIG. 1, but with the excitation and barrier filters of the present invention, and in which the dotted line represents the estimated lens autofluorescence as induced by the excitation wavelengths used in the new filter set.

The present approach provides the ability to take autofluorescence images with a fundus camera using high quality thin film optical interference filters. This new filter set, the spectral characteristics of one embodiment of which are shown in FIG. 5, is much improved over my previously published apparatus, described in reference 15 and shown in FIG. 3. The excitation filter has been selected to mimic the function of a green monochromatic filter. Lipofuscin can absorb a range of 300 nm. to more than 750 nm, however many ranges of these wavelengths occupy regions used for other types of ocular imaging. The wavelengths of the excitation filter are 535 to 585 nm (501), not within the absorption curve of fluorescein, so that autofluorescence photography can be performed on a patient who has had fluorescein angiography. The wavelengths selected are not efficient at causing crystalline lens autofluorescence, a potential source of signal degradation. In FIG. 5 the dotted line represents the lens autofluorescence expected with the new excitation filter. The barrier filter was selected to avoid any crosstalk with the excitation filter. There is a variation in the manufacture of filters and while the transitions between blocking and transmission is steep for modern filters, there still is a slope. The top portion of the curves often extend 10 nm greater than the specified bandwidth, but the transmission is attenuated in these regions by greater than 3 OD. This limits placing the lower edge of the excitation filter much less than about 20 nm from the upper edge of the barrier filter to avoid any cross-talk between the filters. The barrier filter is therefore designed to allow passage of wavelengths starting around 605 nm (502). With this separation it is estimated that there less than $10^{-7}$ of the reflected light from excitation filter coming from the fundus through the barrier filter. The lower portion of the bandpass is limited by the diminishing amount of light available from the fluorescence of lipofuscin and the decrease in resolution and optical performance as the wavelength increases. The barrier filter also blocks passage of longer wavelength infra-red light to avoid image degradation.

The previously published filter set required the camera to be set to have a flash of 300 watt-seconds and a gain on the CCD had to be set to a maximum of 24 dB. With these settings the images were quite dim. The embodiment of the present invention described above requires 200 watt-seconds the flash exposure with the gain set at 20 dB. This results in less patient discomfort and also less noise in the images. The images also are much brighter. Since the camera is optimized for the visible spectrum, shifting the recorded wavelengths up into the visible spectrum improves the optical performance.

The filter selection in the preferred embodiment has important additional benefits. Because of the increased brightness of the image a non-cooled CCD camera can be used, which costs less than a cooled camera. The present system is able to obtain images with a 50 degree field of view and so represents the only system available with a field of view of 30 degrees or greater. Wide-angle imaging allows evaluation of greater expanses of the ocular fundus. Many diseases are recognized and graded on their effects on the fundus. The ability to image larger areas without the need for post-imaging processing and "stitching" of images allows for improved diagnostic capabilities. The wide-angle imaging, along with the ability to image fluorophores in the retina allow for a use of the camera system for "mapping" fundus abnormalities. In diseases causing retinal detachment, such as central serous chorioretinopathy the topographic distribution of areas of detachment can accurately be mapped using the present embodiment. Areas of atrophy or other abnormalities of the retinal pigment epithelium can be mapped topographically as well. Because the wavelengths used in the present embodiment are not influenced by macular pigment, accurate imaging of changes, particularly geographic atrophy, may be performed of the central macula.

The use of a flash to instantaneously record the image is easier for the patient. With the commercially available scanning laser opthalmoscopic system the patient must endure many seconds of uncomfortably bright light for the system to acquire an image.

Monochromatic light (usually green) is used to image the eye. This is usually accomplished by using a green piece of glass as the filter. The green light used is absorbed by blood and enables improved contrast when imaging the retina. The new excitation filter used in this system is green in color and can be used to replace the green filter. The barrier filter is deep red in color. Imaging the fundus with deep red wavelengths provides the ability of imaging subretinal structures. To perform monochromatic photographs the excitation filter is used, for deep-red the barrier filter is used, and for autofluorescence photography both are used.

Fundus cameras have a limited number of filter slots, making implementation of this system easy for many models of fundus cameras. The previously published filter arrangement had an excitation filter that had no other use. Fundus cameras often have no open slot for excitation filters, which meant that to add autofluorescence to a fundus camera the owner had to give up some other function, such as either fluorescein or indocyanine green angiography. Autofluorescence imaging can also be used to estimate the amount of macular pigment. An autofluorescent photograph is taken with the filter set described. An additional photograph is taken with a blue filter with a bandpass of about 450-490 nm. The normal autofluorescent photograph is divided by the autofluorescent photograph taken through the blue filter. This gives an image where the grayscale value is proportional to the amount of lipofuscin present. The graphical display of the resultant image is then done in a process similar to that described in my copending U.S. patent application entitled "Reflectance Measurement of Macular Pigment Using Multispectral Imaging," U.S. Application Ser. No. 60/913,885, which is incorporated herein by reference.

Figure 6:
FIG. 6 is an example of an autofluorescence photograph taken with the new system of a patient with Stargardt disease.

FIG. 6 is an example of an autofluorescence photograph taken with the new system. Stargardt disease is caused by a mutation in the ABCA4 gene and causes visual acuity loss with age. Autofluorescence photography shows increased background autofluorescence and hyperautofluorescence of the yellow flecks commonly found in this disorder. With time patchy atrophy develops in the fundus and geographic atrophy occurs in the central macula. The geographic atrophy can lead to profound vision loss. The areas of cell death, which are very difficult to appreciate with ordinary opthalmoscopic examination or color photography, are black because of the lack of cells containing lipofuscin.

There are several other improvements over prior art for autofluorescence imaging with a fundus camera. Because the specified wavelengths of the exciter filter is green in color the excitation filter can be used in the filter slot ordinarily reserved for the commonly used green filter used in monochromatic fundus photography. The barrier filter transmission band is placed in a zone closer to the peak emission of lipofuscin. The filters used have high levels of transmission in the passband and rejection of wavelengths outside of the region selected. Because of these factors other image brightness is approximately an order of magnitude greater than the previously published filter set (Spaide R F, Opthalmology 2003). Because of the greater brightness less excitation light is needed, a lower gain can be used for the camera, and a non-cooled CCD can be employed, and wide-angle imaging can be utilized. There is an increased safety profile of the excitation light used in the present embodiment as compared with that used in commercially available scanning laser opthalmoscopic system, which uses excitation wavelengths shorter than 530 nm., which are known to excite photochemical reactions of lipofuscin. The excitation filter as specified does not stimulate fluorescein, allowing greater flexibility in the workflow of an opthalmologist's office in that autofluorescence photographs can be taken as needed, both before and after fluorescein angiography. The wavelengths used for excitation are not absorbed by macular pigment providing a method to evaluate the central macula.

While the presently preferred embodiments have been described in detail, it will be apparent to those skilled in the art that the principles of the invention are realizable by other devices and methods without departing from the scope and spirit of the invention, as defined in the following claims.

I claim:

1. A method of taking a monochromatic image of an eye, comprising the steps of:
    emitting an excitation light;
    filtering the excitation light through a band-pass filter having a band-pass range of about 535-585 nm;
    directing the filtered excitation light into an eye; and
    taking an image of the eye with a fundus camera.

2. A method of taking an image of sub-retinal structures of an eye, comprising the steps of:
    emitting an excitation light:
    directing the excitation light into an eye:
    filtering light emitted from the eye through a band-pass filter having a band-pass range of about 605-715 nm; and
    taking an image of the eye with a fundus camera.

3. An ophthalmic method for diagnosing conditions in an eye, comprising the steps of:
    emitting an excitation light;
    filtering the excitation light through an excitation filter having an excitation cut-on wavelength, an excitation cut-off wavelength, and an excitation band-pass range, wherein the excitation band-pass range is selected to:
        excite fluorescence from a fluorophore present in an eye;
        substantially avoid the absorption range of fluorescein;
        substantially avoid the absorption range of indocyanine green dye;
        substantially avoid the absorption range of macular pigment; and
        limit excitation of fluorescence from a crystalline lens;
    directing the filtered excitation light into the eye;
    collecting the fluorescence emitted from the fluorophore within a field of view of the fundus of the eye;
    filtering the collected fluorescence through a barrier filter having a barrier cut-on wavelength, a barrier cut-off wavelength, and a barrier band-pass range; and
    generating an image based at least in part on the filtered fluorescence.

4. The method of claim 3 wherein the field of view is at least 30 degrees.

5. The method of claim 3 wherein the field of view is at least 50 degrees.

6. The method of claim 3, wherein the excitation band-pass range does not excite damaging photochemical reactions involving lipofuscin.

7. The method of claim 3 further comprising the step of:
    detecting significant accumulation of fluorophores in a retina prior to significant accumulation of fluorophores in a retinal pigment epithelium.

8. The method of claim 3, further comprising the step of:
    topographically localizing and quantitating the size of retinal abnormalities.

9. The method of claim 3, further comprising the step of:
    topographically localizing and quantitating the size of abnormalities of a retinal pigment epithelium.

10. The method of claim 3, further comprising the step of:
    capturing the image with a fundus camera.

11. The method of claim 10 wherein the fundus camera comprises a charge coupled device.

12. The method of claim 11 wherein the charge coupled device is non-cooled.

13. The method of claim 3, further comprising the step of:
    imaging a central macula without substantial inhibition by macular pigment.

14. The method of claim 3, further comprising the step of:
    assessing the amount of geographic atrophy in a central macula.

15. The method of claim 3, wherein the barrier cut-on wavelength is:
    longer than the excitation cut-off wavelength;
    separated in wavelength from the excitation cut-off wavelength by an amount sufficient to avoid crosstalk between the excitation filter and the barrier filter; and
    longer than the peak fluorescence emission range of the crystalline lens.

16. The method of claim 3, wherein the excitation filter and the barrier filter are interferometric filters.

17. The method of claim 3, wherein:
    the excitation band-pass range is about 535-585 nm; and
    the barrier band-pass range is about 605-715 nm.

18. The method of claim 3 wherein the barrier and excitation filters have a rejection of at least $10^7$.

19. The method of claim 3, wherein the fluorophore is lipofuscin.

20. An apparatus for taking an auto fluorescence image of an eye, comprising:
    a fundus camera;
    an excitation filter having an excitation cut-on wavelength, an excitation cut-off wavelength, and an excitation band-pass range, wherein the excitation band-pass range is selected to:
        excite fluorescence from a fluorophore present in an eye;
        substantially avoid the absorption range of fluorescein;
        substantially avoid the absorption range of indocyanine green dye;
        substantially avoid the absorption range of macular pigment; and
        limit excitation of fluorescence from a crystalline lens; and
    a barrier filter having a barrier cut-on wavelength, a barrier cut-off wavelength, and a barrier band-pass range, wherein the barrier cut-on wavelength is:

longer than the excitation cut-off wavelength;

separated in wavelength from the excitation cut-off wavelength by an amount sufficient to avoid crosstalk between the excitation filter and the barrier filter; and longer than the peak fluorescence emission range of the crystalline lens.

21. The apparatus of claim 20, wherein the excitation filter and the barrier filter are interferometric filters.

22. The apparatus of claim 20, wherein the excitation band-pass range is about 535-585 nm and the barrier band-pass range is about 605-715 nm.

23. The apparatus of claim 20, wherein the fundus camera comprises a charge coupled device.

24. The apparatus of claim 23, wherein the charge coupled device is non-cooled.

25. The apparatus of claim 20, wherein the excitation filter comprises a green filter of the fundus camera.

26. The apparatus of claim 20, wherein the fluorophore is lipofuscin.

27. The apparatus of claim 20, wherein the barrier and excitation filters have a rejection of at least $10^7$.

28. A method for estimating an amount of macular pigment in an eye, comprising the steps of:

emitting an excitation light;

filtering the excitation light through a first excitation filter having an excitation band-pass range of about 535-585 nm;

directing the excitation light filtered through the first excitation filter into an eye;

collecting a first fluorescence emitted from a fluorophore within a field of view of the fundus of the eye;

filtering the collected first fluorescence through a barrier filter having a barrier band-pass range of about 605-715 nm;

generating a first image based at least in part on the first fluorescence filtered through the barrier filter;

filtering the excitation light through a second excitation filter having an excitation band-pass range of about 450-490 nm;

directing the excitation light filtered through the second excitation filter into the eye;

collecting a second fluorescence emitted from the fluorophore;

filtering the collected second fluorescence through the barrier filter;

generating a second image based at least in part on the second fluorescence filtered through the barrier filter;

dividing the first image by the second image to produce a grayscale image; and estimating the amount of macular pigment based at least in part on the grayscale image.

* * * * *

UNITED STATES PATENT AND TRADEMARK OFFICE
CERTIFICATE OF CORRECTION

PATENT NO. : 7,648,239 B2
APPLICATION NO. : 11/742672
DATED : January 19, 2010
INVENTOR(S) : Richard Spaide It is certified that error appears in the above-identified patent and that said Letters Patent is hereby corrected as shown below:

Column 1, line 7, "opthalmology" should read --ophthalmology--.

Column 1, lines 25-26, "opthalmoscope" should read --ophthalmoscope--.

Column 2, line 41, "opthalmology" should read --ophthalmology--.

Column 3, line 1, "opthalmoscopes" should read --ophthalmoscopes--.

Column 3, line 5, "opthalmoscope" should read --ophthalmoscope--.

Column 3, lines 5-6, "opthalmoscopes" should read --ophthalmoscopes--.

Column 3, line 22, "opthalmoscope" should read --ophthalmoscope--.

Column 6, line 26, "opthalmoscopic" should read --ophthalmoscopic--.

Column 6, line 30, "Opthalmology" should read --Ophthalmology--.

Column 8, line 18, "opthalmoscopic" should read --ophthalmoscopic--.

Column 8, line 65, "opthalmoscopic" should read --ophthalmoscopic--.

Column 9, line 12, "Opthalmology" should read --Ophthalmology--.

Column 9, line 19, "opthalmoscopic" should read --ophthalmoscopic--.

Column 9, line 23, "opthalmologist's" should read --ophthalmologist's--.

Column 9, line 43 (Claim 2, line 3), "light:" should read --light;--.

Column 9, line 44 (Claim 2, line 4), "eye:" should read --eye;--.

Signed and Sealed this

Twenty-third Day of March, 2010

David J. Kappos
*Director of the United States Patent and Trademark Office*